United States Patent
Fujii et al.

(10) Patent No.: US 11,317,818 B2
(45) Date of Patent: May 3, 2022

(54) BLOOD PRESSURE MEASUREMENT DEVICE AND BLOOD PRESSURE MEASUREMENT METHOD

(71) Applicants: OMRON CORPORATION, Kyoto (JP); OMRON HEALTHCARE CO., LTD., Muko (JP)

(72) Inventors: Kenji Fujii, Kyoto (JP); Naoki Matsumoto, Kyoto (JP); Yuki Kato, Kyoto (JP)

(73) Assignees: OMRON CORPORATION, Kyoto (JP); OMRON HEALTHCARE CO., LTD., Kyoto (JP)

(*) Notice: Subject to any disclaimer, the term of this patent is extended or adjusted under 35 U.S.C. 154(b) by 350 days.

(21) Appl. No.: 16/448,145

(22) Filed: Jun. 21, 2019

(65) Prior Publication Data

US 2019/0307340 A1    Oct. 10, 2019

Related U.S. Application Data

(63) Continuation of application No. PCT/JP2017/038869, filed on Oct. 27, 2017.

(30) Foreign Application Priority Data

Dec. 28, 2016    (JP) .............................. JP2016-254772

(51) Int. Cl.
*A61B 5/022*    (2006.01)
*A61B 5/02*    (2006.01)
(Continued)

(52) U.S. Cl.
CPC ............ *A61B 5/02225* (2013.01); *A61B 5/02* (2013.01); *A61B 5/022* (2013.01);
(Continued)

(58) Field of Classification Search
CPC ........ A61B 5/02; A61B 5/681; A61B 5/02125
See application file for complete search history.

(56) References Cited

U.S. PATENT DOCUMENTS 5,582,179 A    12/1996    Shimizu et al.
5,649,543 A    7/1997    Hosaka et al.
(Continued)

FOREIGN PATENT DOCUMENTS

JP    H07-124129 A    5/1995
JP    H07-327940 A    12/1995
(Continued)

OTHER PUBLICATIONS

Dec. 19, 2017 International Search Report issued in International Patent Application No. PCT/JP2017/038869.
(Continued)

*Primary Examiner* — Puya Agahi
(74) *Attorney, Agent, or Firm* — Oliff PLC

(57) ABSTRACT

A belt to be mounted around a measurement site; first pulse wave sensor and second pulse wave sensor mounted on the belt, separated from each other, configured to detect pulse waves in an artery passing through the measurement site; and pressing member mounted on the belt, capable of pressing first pulse wave sensor and second pulse wave sensor against the measurement site while varying pressing force. Time difference between first and second pulse wave signals is acquired as pulse transit time. Blood pressure is calculated based on the pulse transit time acquired by the measurement processing unit by using a predetermined correspondence equation between pulse transit time and
(Continued)

blood pressure. Pulse transit time is acquired with the measurement processing unit while pressing force by pressing member is changed in resting state, and corresponding equation is calibrated based on plurality of pulse transit times corresponding to plurality of respective pressing forces.

6 Claims, 11 Drawing Sheets

(51) Int. Cl.
*A61B 5/0285* (2006.01)
*A61B 5/00* (2006.01)
*A61B 5/021* (2006.01)
*A61B 5/0245* (2006.01)
*A61B 5/053* (2021.01)

(52) U.S. Cl.
CPC ........ *A61B 5/02007* (2013.01); *A61B 5/0285* (2013.01); *A61B 5/681* (2013.01); *A61B 5/6831* (2013.01); *A61B 5/0245* (2013.01); *A61B 5/02108* (2013.01); *A61B 5/02125* (2013.01); *A61B 5/053* (2013.01); *A61B 5/6824* (2013.01); *A61B 5/7275* (2013.01)

(56) References Cited

U.S. PATENT DOCUMENTS

| | | | |
|---|---|---|---|
| 2010/0076328 A1* | 3/2010 | Matsumura | A61B 5/6843 600/500 |
| 2010/0241011 A1 | 9/2010 | McCombie et al. | |
| 2012/0136261 A1* | 5/2012 | Sethi | A61B 5/1495 600/485 |
| 2014/0073864 A1* | 3/2014 | Engelbrecht | A61B 5/7228 600/301 |
| 2015/0073230 A1 | 3/2015 | Stergiou | |
| 2015/0238095 A1 | 8/2015 | Lading et al. | |

FOREIGN PATENT DOCUMENTS

| | | |
|---|---|---|
| JP | H10-328151 A | 12/1998 |
| JP | 2015-54237 A | 3/2015 |
| JP | 5984088 B2 | 9/2016 |
| WO | 2015/127135 A1 | 8/2015 |
| WO | WO-2016040253 A1 * | 3/2016 ........... A61B 5/6824 |

OTHER PUBLICATIONS

Teng et al. "Theoretical Study on the Effect of Sensor Contact Force on Pulce Transit Time." IEEE Transactions on Biomedical Engineering, 2007, vol. 54, No. 8, pp. 1490-1498.

May 24, 2021 Office Action issued in Chinese Patent Application No. 201780077126.0.

* cited by examiner

FIG.11B
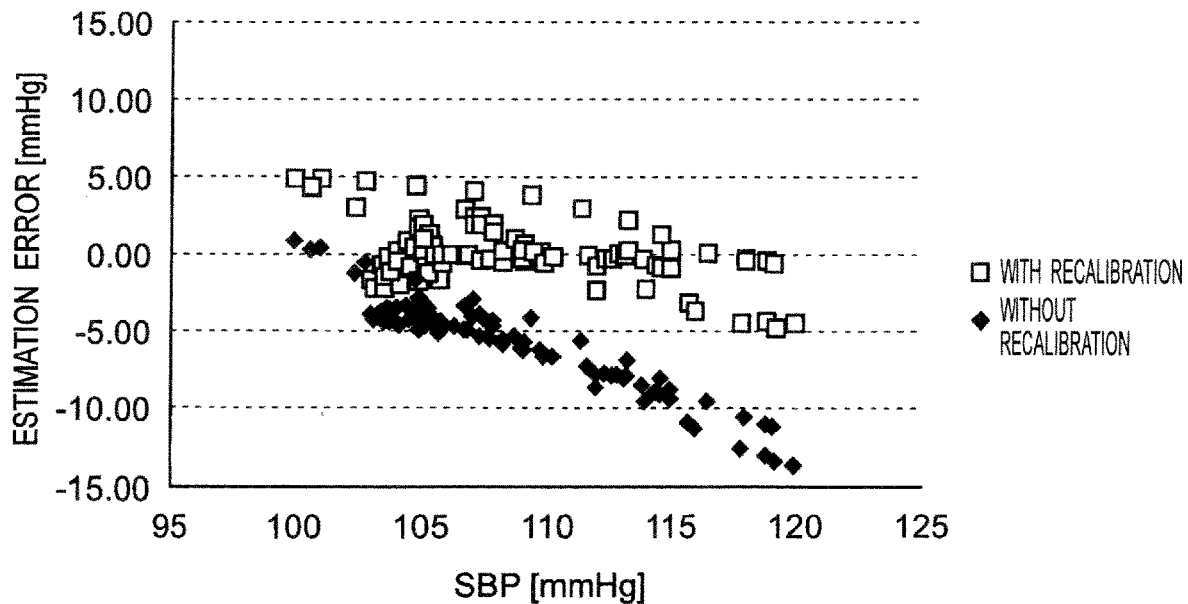
FIG.12
$$r = \frac{\sum_{i=1}^{n}(x_i - \bar{x})(y_i - \bar{y})}{\left\{\left(\sum_{i=1}^{n}(x_i - \bar{x})^2\right)\left(\sum_{i=1}^{n}(y_i - \bar{y})^2\right)\right\}^{1/2}} \quad \cdots (Eq.1)$$
FIG.13
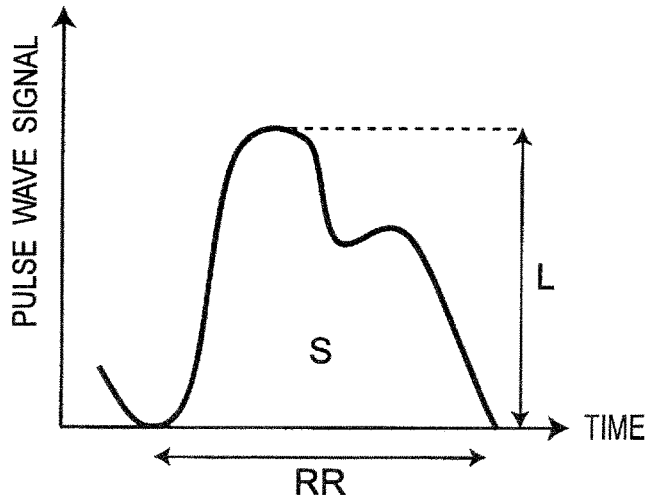

BLOOD PRESSURE MEASUREMENT DEVICE AND BLOOD PRESSURE MEASUREMENT METHOD

CROSS-REFERENCE TO RELATED APPLICATION

This is a continuation application of International Application No. PCT/JP2017/038869, with an International filing date of Oct. 27, 2017, which claims priority of Japanese Patent Application No. 2016-254772 filed on Dec. 28, 2016, the entire content of which is hereby incorporated by reference.

TECHNICAL FIELD

The present invention relates to a blood pressure measurement device and a blood pressure measurement method, and more specifically, a blood pressure measurement device and a blood pressure measurement method for measuring blood pressure based on the transit time of pulse waves propagating in an artery (pulse transit time; PTT).

BACKGROUND ART

Conventionally, there has been proposed a method of calculating blood pressure by using the correspondence relationship between the transit time of pulse waves propagating through the blood vessel wall in accordance with the pulsation of the heart and the blood pressure (for example, see Patent Literature 1; U.S. Pat. No. 5,984,088). The correspondence relationship between this pulse transit time and the blood pressure is different for each subject, and it is necessary to calibrate correspondence equations different for each individual.

Patent Literature 1 discloses a noninvasive continuous blood pressure monitoring device for performing continuous blood pressure measurement under free action in a subject's daily life by using a wearable biological sensor. The blood pressure monitoring device of Patent Literature 1 acquires a pulse transit time from a biosignal, and calculates the blood pressure by using the acquired pulse transit time and a blood pressure calculation equation based on a constant parameter. In order to calibrate such a blood pressure calculation equation, in Patent Literature 1, parameter calibration using exercise stress on a subject and parameter calibration using mental stress are performed.

SUMMARY OF INVENTION

As disclosed in Patent Literature 1, in the conventional method, in order to calibrate the correspondence equation between the pulse transit time and the blood pressure, it is necessary to simultaneously measure the pulse transit time and the blood pressure while fluctuating the blood pressure with the exercise stress or the mental stress. For this reason, in the conventional method, there is a problem that an excessive burden is placed on the subject or it takes time for calibration when the calibration of the corresponding equation for blood pressure measurement based on the pulse transit time is performed.

Thus, an object of the present invention is to provide a blood pressure measurement device and a blood pressure measurement method capable of facilitating calibration when blood pressure is measured based on a pulse transit time.

Solutions to Problems

In order to solve the above-mentioned problem, a blood pressure measurement device of the present disclosure comprises:

a belt to be mounted around a measurement site;

a first pulse wave sensor and a second pulse wave sensor mounted on the belt in a state of being separated from each other in a width direction of the belt, the first pulse wave sensor and the second pulse wave sensor being configured to detect pulse waves of respective portions facing the first pulse wave sensor and the second pulse wave sensor of an artery passing through the measurement site;

a measurement processing unit configured to acquire, as a pulse transit time, a time difference between a first pulse wave signal and a second pulse wave signal respectively output by the first pulse wave sensor and the second pulse wave sensor in time series;

a first blood pressure calculation unit configured to use a predetermined correspondence equation between a pulse transit time and a blood pressure to calculate a blood pressure based on a pulse transit time acquired by the measurement processing unit;

a pressing member mounted on the belt, configured to press the first pulse wave sensor and the second pulse wave sensor against the measurement site while varying a pressing force; and a calibration processing unit configured to acquire a pulse transit time with the measurement processing unit while changing a pressing force by the pressing member in a resting state to calibrate the corresponding equation based on a plurality of pulse transit times corresponding to a plurality of respective pressing forces.

In the present specification, "measurement site" refers to a site through which an artery passes. The measurement site may be, for example, an upper limb such as a wrist or an upper arm, or a lower limb such as an ankle or a thigh.

In addition, "belt" refers to a band-shaped member mounted around a measurement site regardless of the name. For example, instead of the belt, the name may be "band", "cuff", or the like.

In addition, "resting state" refers to a state in which the pulse rate (beat/minute) of the subject having the measurement site does not fluctuate excessively. For example, the resting state is a state in which the fluctuation amount of the pulse rate (for example, standard deviation of 10 seconds) is 5 beat/minute or less.

In addition, "predetermined correspondence equation between pulse transit time and blood pressure" refers to, for example, the following equation disclosed in Non-Patent Literature 1; X. F. T. Teng, Y. T. Zhang, "Theoretical Study on the Effect of Sensor Contact Force on Pulse Transit Time", IEEE Transactions on Biomedical Engineering, Vol. 54, No. 8, pp. 1490-1498, 2007.

[Mathematical Equation 1]

$$PTT = a \cdot \exp[-b(Pi-Po)] + c \quad (Eq)$$

where PTT represents a pulse transit time, and Pi represents a blood pressure value to be calculated, Po represents a pressure value due to external pressure such as pressing force by the pressing member. a, b, and c are coefficients.

In addition, to "calibrate" the correspondence equation refers to setting the coefficients a, b, and c by using a measured pulse transit time and blood pressure value, for example, in the case of the correspondence equation (Eq) exemplified above.

In another aspect, a blood pressure measurement method of the present disclosure is a blood pressure measurement method includes:

using
a belt to be mounted around a measurement site,
a first pulse wave sensor and a second pulse wave sensor mounted on the belt in a state of being separated from each other in a width direction of the belt, the first pulse wave sensor and the second pulse wave sensor being configured to detect pulse waves of respective portions facing the first pulse wave sensor and the second pulse wave sensor of an artery passing through the measurement site, and
a pressing member mounted on the belt, configured to press the first pulse wave sensor and the second pulse wave sensor against the measurement site while varying a pressing force,
to measure a blood pressure based on a pulse wave of the measurement site, the blood pressure measurement method comprising:
acquiring, as a pulse transit time, a time difference between a first pulse wave signal and a second pulse wave signal respectively output by the first pulse wave sensor and the second pulse wave sensor in time series while changing a pressing force by the pressing member in a resting state;
calibrating a predetermined correspondence equation between a pulse transit time and a blood pressure based on a plurality of pulse transit times corresponding to a plurality of respective pressing forces; and
calculating a blood pressure based on the pulse transit time by using the correspondence equation.

BRIEF DESCRIPTION OF DRAWINGS

The present invention will become more fully understood from the detailed description given hereinbelow and the accompanying drawings which are given by way of illustration only, and thus are not limitative of the present invention, and wherein:

FIG. 11B is a scatter diagram illustrating distribution of estimation errors corresponding to the presence or absence of calibration of the correspondence equation when the measurement conditions change.

FIG. 12 is a diagram illustrating an equation representing a cross-correlation coefficient r between a data sequence {xi} and a data sequence {yi}.

FIG. 13 is a waveform diagram illustrating the waveform of a pulse wave for describing a plethysmogram area ratio.

DESCRIPTION OF EMBODIMENTS

Hereinafter, embodiments of the present invention will be described in detail with reference to the drawings.
(Configuration of Sphygmomanometer)

Figure 1:
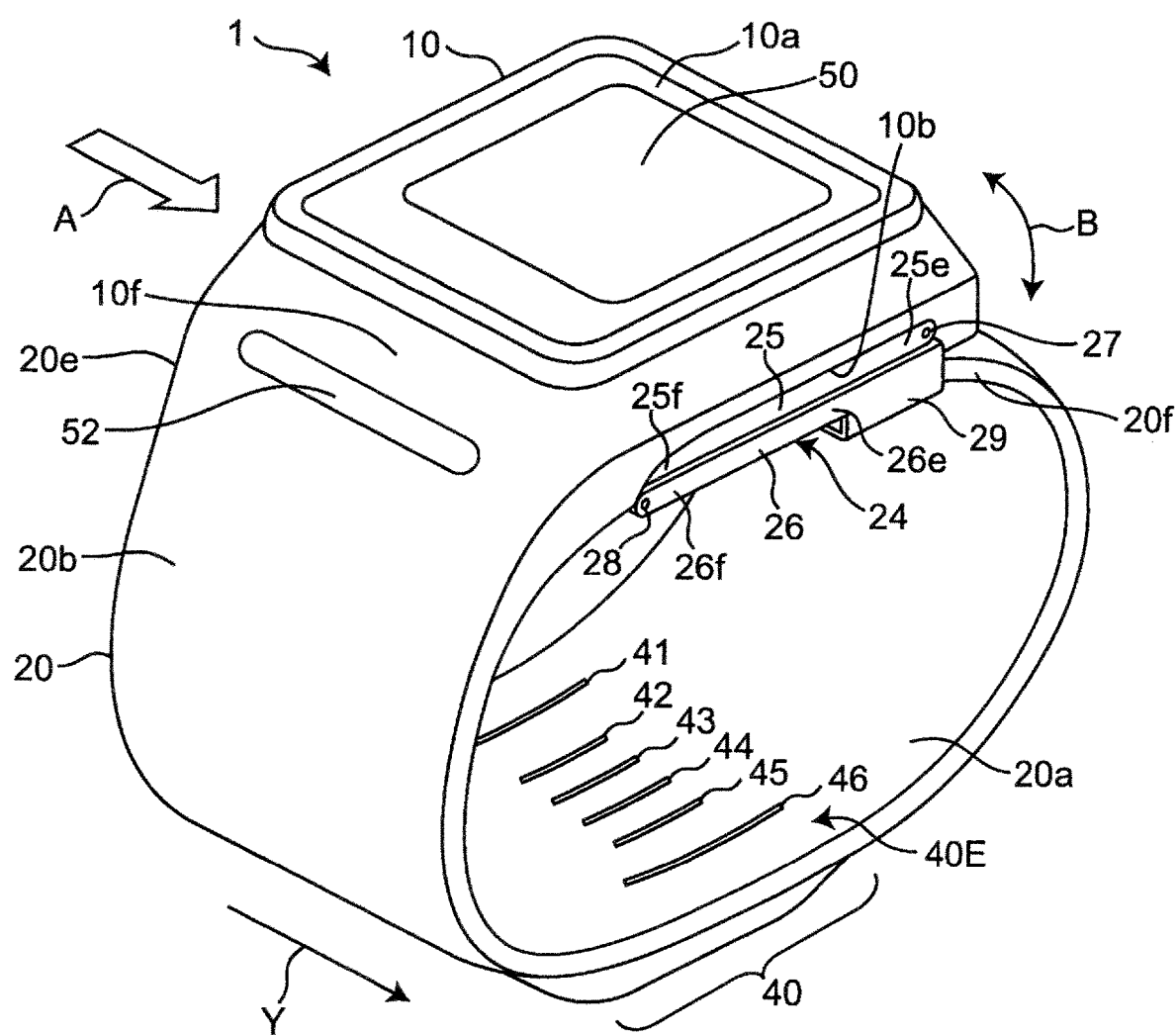
FIG. 1 is a perspective view illustrating the appearance of a wrist-type sphygmomanometer of one embodiment according to a blood pressure measurement device including a pulse wave measurement device of the present invention.
Figure 2:
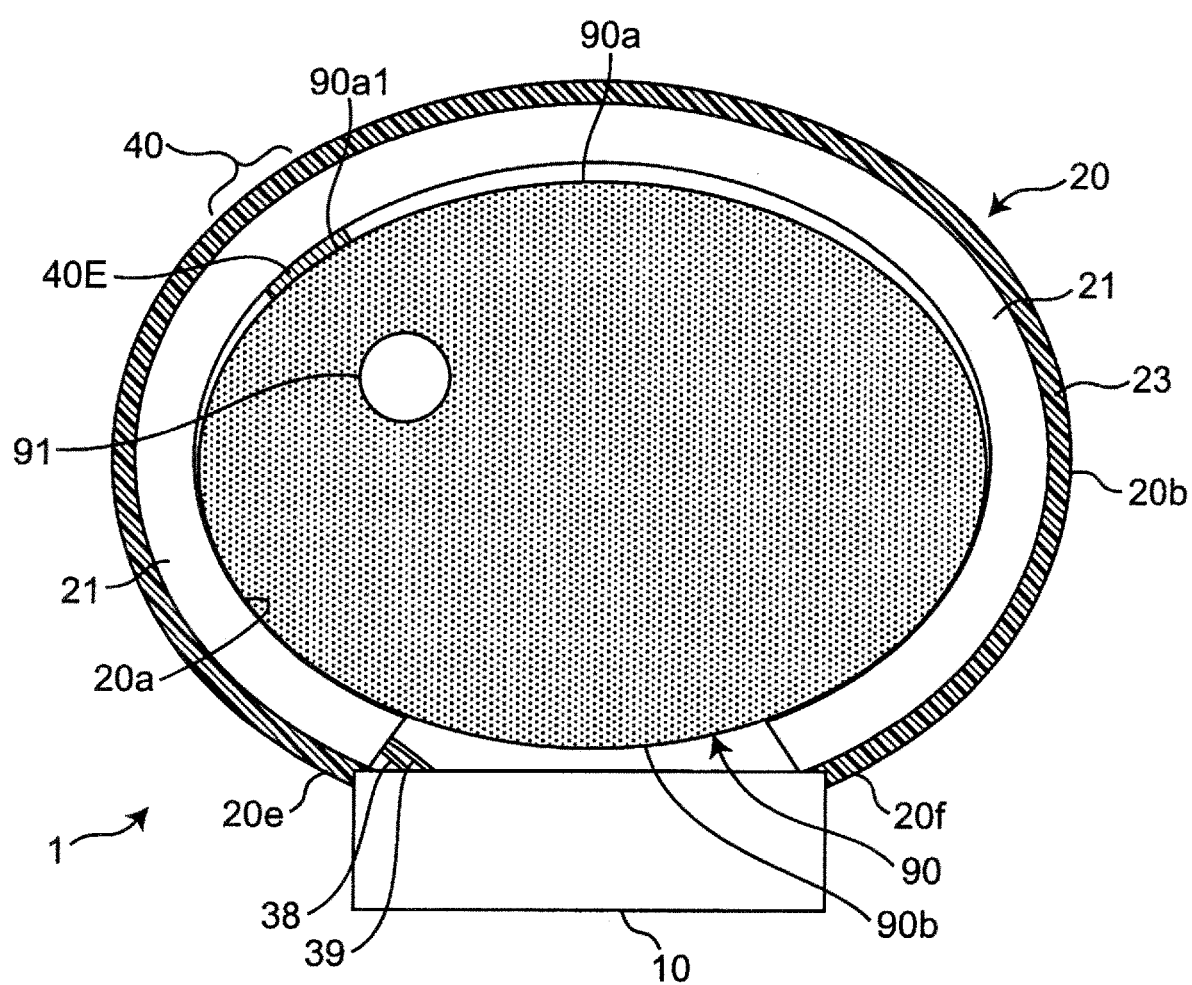
FIG. 2 is a diagram schematically illustrating a cross section perpendicular to the longitudinal direction of the wrist in a state where the sphygmomanometer is mounted on the left wrist.

FIG. 1 illustrates the appearance of a wrist-type sphygmomanometer (the whole is denoted by reference numeral 1) of one embodiment according to a blood pressure measurement device including a pulse wave measurement device of the present invention as viewed from an oblique direction. In addition, FIG. 2 schematically illustrates a cross section perpendicular to the longitudinal direction of the left wrist 90 in a state where the sphygmomanometer 1 is mounted on the left wrist 90 as a measurement site (hereinafter referred to as "mounted state").

As illustrated in these drawings, the sphygmomanometer 1 roughly includes a belt 20 to be worn around a user's left wrist 90 and a main body 10 integrally attached to the belt 20.

As well understood from FIG. 1, the belt 20 has an elongated belt shape to surround the left wrist 90 along the circumferential direction, an inner peripheral surface 20a to be in contact with the left wrist 90, and an outer peripheral surface 20b on the opposite side of the inner peripheral surface 20a. The dimension (width dimension) in the width direction Y of the belt 20 is set to about 30 mm in this example.

The main body 10 is integrally provided at one end portion 20e of the belt 20 in the circumferential direction by integral molding in this example. It should be noted that the belt 20 and the main body 10 may be separately formed, and the main body 10 may be integrally attached to the belt 20 via an engaging member (for example, a hinge or the like). In this example, the site where the main body 10 is disposed is intended to correspond to the back side surface of the left wrist 90 (the surface on the back side of the hand) 90b in the mounted state (see FIG. 2). In FIG. 2, a radial artery 91 passing near the palmar surface (the surface on the palmar side) 90a in the left wrist 90 is illustrated.

As well understood from FIG. 1, the main body 10 has a three-dimensional shape having a thickness in a direction perpendicular to the outer peripheral surface 20b of the belt 20. The main body 10 is formed small and thin so as not to interfere with the daily activities of the user. In this example, the main body 10 has a truncated quadrangular pyramid-shaped contour projecting outward from the belt 20.

A display 50 serving as a display screen is provided on the top surface of the main body 10 (the surface on a side farthest from the measurement site) 10a. In addition, an operation unit 52 for inputting instructions from the user is provided along the side surface 10f of the main body 10 (side surface on the left front side in FIG. 1).

An impedance measurement unit 40 constituting first and second pulse wave sensors is provided in a site between one end portion 20e and the other end portion 20f in the circumferential direction of the belt 20. Of the belt 20, on the inner peripheral surface 20a of the site where the impedance measurement unit 40 is disposed, six plate-shaped (or sheet-shaped) electrodes 41 to 46 (all of which are referred to as "electrode group" and denoted by reference numeral 40E) are arranged in a state of being separated from each other in the width direction Y of the belt 20 (described in detail below). In this example, the site where the electrode group 40E is disposed is intended to correspond to the radial artery 91 of the left wrist 90 in the mounted state (see FIG. 2).

As illustrated in FIG. 1, the bottom surface of the main body 10 (the surface on the side closest to the measurement site) 10b and the end portion 20f of the belt 20 are connected by a threefold buckle 24. The buckle 24 includes a first plate-shaped member 25 disposed on the outer peripheral side and a second plate-shaped member 26 disposed on the inner peripheral side. One end portion 25e of the first plate-shaped member 25 is rotatably attached to the main body 10 via a coupling rod 27 extending along the width direction Y. The other end portion 25f of the first plate-shaped member 25 is rotatably attached to one end portion 26e of the second plate-shaped member 26 via a coupling rod 28 extending along the width direction Y. The other end portion 26f of the second plate-shaped member 26 is fixed near the end portion 20f of the belt 20 by the fixing portion 29. It should be noted that the attaching position of the fixing portion 29 in the circumferential direction of the belt 20 is variably set in advance in accordance with the circumferential length of the left wrist 90 of the user. Thus, the sphygmomanometer 1 (belt 20) is formed in a substantially annular shape as a whole, and the bottom surface 10b of the main body 10 and the end portion 20f of the belt 20 can be opened and closed in the arrow B direction by the buckle 24.

When mounting the sphygmomanometer 1 on the left wrist 90, the user inserts the left hand into the belt 20 in the direction indicated by the arrow A in FIG. 1 with the buckle 24 open and the diameter of the ring of the belt 20 increased. Then, as illustrated in FIG. 2, the user adjusts the angular position of the belt 20 around the left wrist 90 to position the impedance measurement unit 40 of the belt 20 on the radial artery 91 passing through the left wrist 90. Thus, the electrode group 40E of the impedance measurement unit 40 abuts on a portion 90a1 corresponding to the radial artery 91 on the palmar surface 90a of the left wrist 90. In this state, the user closes and fixes the buckle 24. Thus, the user wears the sphygmomanometer 1 (belt 20) on the left wrist 90.

As illustrated in FIG. 2, in this example, the belt 20 includes a strip 23 forming the outer peripheral surface 20b and a pressing cuff 21 as a pressing member attached along the inner peripheral surface of the strip 23. The strip 23 is, in this example, made of a plastic material that is flexible in the thickness direction and substantially non-stretchable in the circumferential direction (longitudinal direction). In this example, the pressing cuff 21 is configured as a fluid bag by facing two stretchable polyurethane sheets in the thickness direction and welding their peripheral portions. The electrode group 40E of the impedance measurement unit 40 is disposed at a site corresponding to the radial artery 91 of the left wrist 90 on the inner peripheral surface 20a of the pressing cuff 21 (belt 20) as described above.

Figure 3:
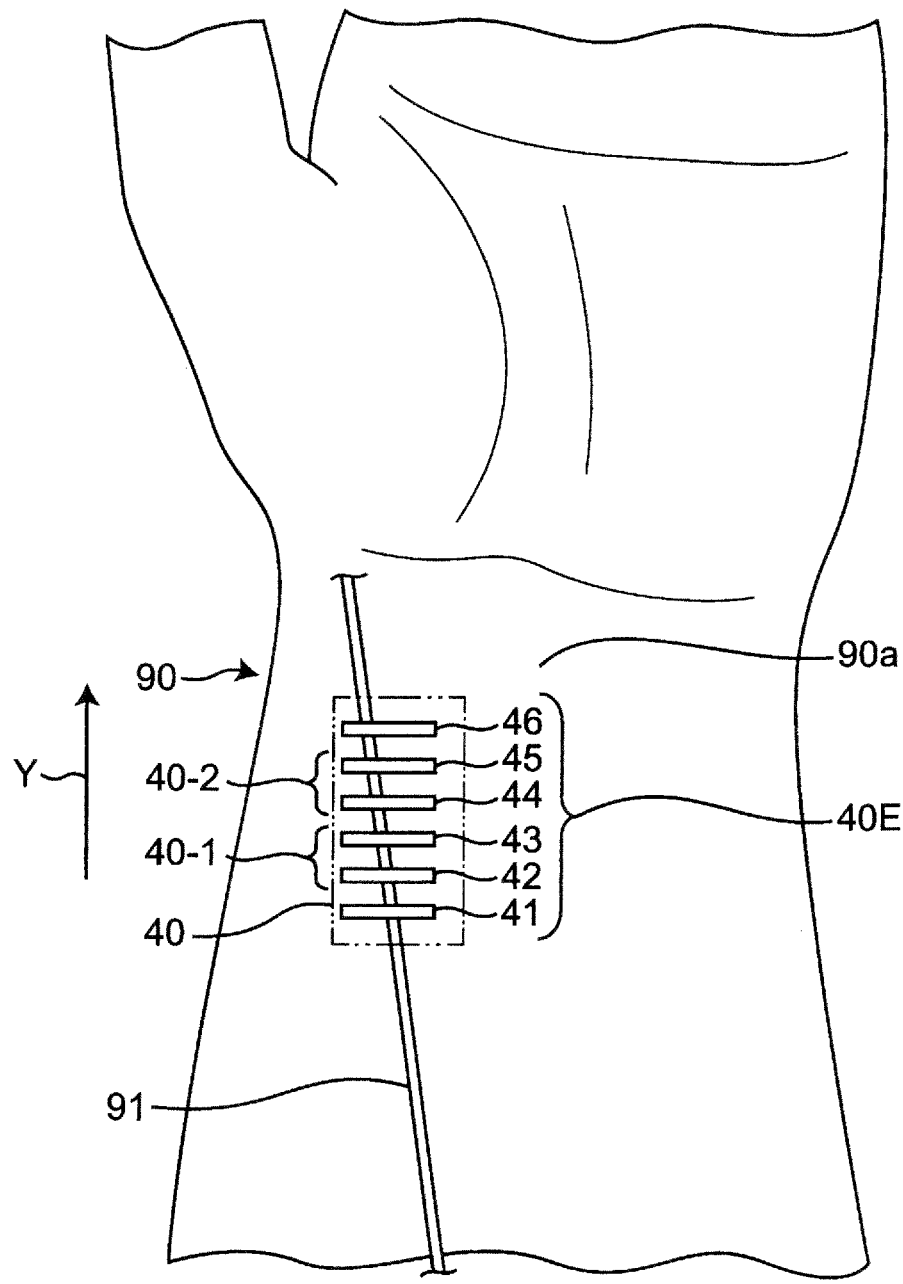
FIG. 3 is a diagram illustrating a planar layout of impedance measurement electrodes constituting first and second pulse wave sensors in a state where the sphygmomanometer is mounted on the left wrist.

As illustrated in FIG. 3, in the mounted state, the electrode group 40E of the impedance measurement unit 40 is aligned along the longitudinal direction of the wrist (corresponding to the width direction Y of the belt 20) according to the radial artery 91 of the left wrist 90. The electrode group 40E includes a current electrode pair 41 and 46 for energization disposed on both sides in the width direction Y, a first detection electrode pair 42 and 43 forming a first pulse wave sensor 40-1 for voltage detection disposed between the current electrode pair 41 and 46, and a second detection electrode pair 44 and 45 forming a second pulse wave sensor 40-2. With respect to the first detection electrode pair 42 and 43, the second detection electrode pair 44 and 45 is disposed according to the portion on the more downstream side of the blood flow of the radial artery 91. In the width direction Y, the distance D between the center of the first detection electrode pair 42 and 43 and the center of the second detection electrode pair 44 and 45 (see FIG. 5A) is set to 20 mm in this example. This distance D corresponds to a substantial space between the first pulse wave sensor 40-1 and the second pulse wave sensor 40-2. In addition, in the width direction Y, the space between the first detection electrode pair 42 and 43 and the space between the second detection electrode pair 44 and 45 are both set to 2 mm in this example.

This electrode group 40E can be configured to be flat. Therefore, in the sphygmomanometer 1, the belt 20 can be configured to be thin as a whole.

Figure 4:
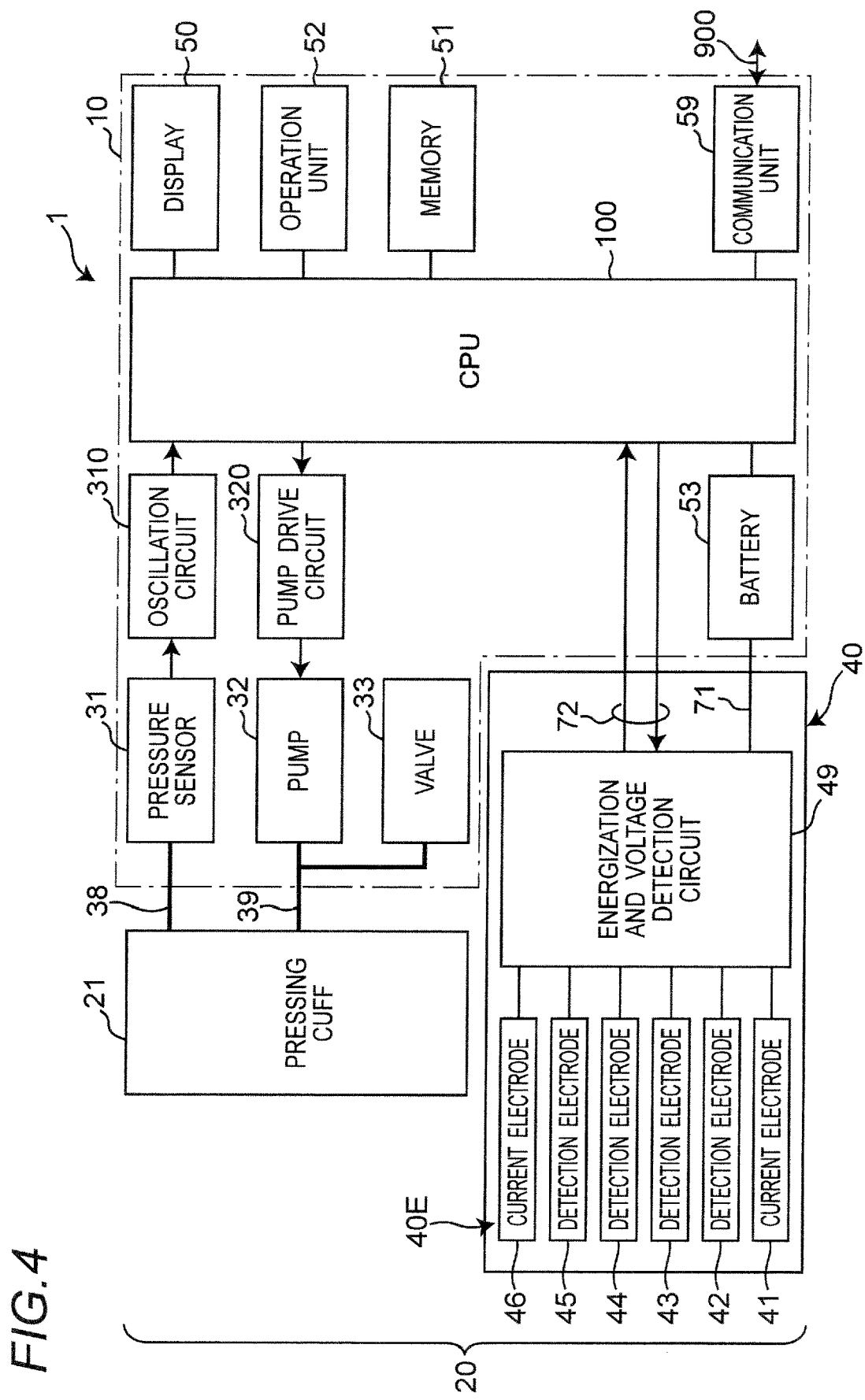
FIG. 4 is a diagram illustrating a block configuration of a control system of the sphygmomanometer.

FIG. 4 illustrates a block configuration of a control system of the sphygmomanometer 1. In addition to the display 50 and the operation unit 52 described above, the main body 10 of the sphygmomanometer 1 mounts a central processing unit (CPU) 100 as a control unit, a memory 51 as a storage unit, a communication unit 59, a pressure sensor 31, a pump 32, a valve 33, an oscillation circuit 310 for converting the output from the pressure sensor 31 into a frequency, and a pump drive circuit 320 for driving the pump 32. Furthermore, in addition to the electrode group 40E described above, the impedance measurement unit 40 mounts an energization and voltage detection circuit 49.

The display 50 includes an organic electro luminescence (EL) display in this example, and displays information related to blood pressure measurement such as blood pressure measurement results and other information in accordance with a control signal from the CPU 100. It should be noted that the display 50 is not limited to the organic EL display, and may include another type of display such as a liquid crystal display (LCD).

The operation unit 52 includes a push switch in this example, and inputs an operation signal corresponding to the user's instructions to start or stop blood pressure measurement into the CPU 100. It should be noted that the operation unit 52 is not limited to the push switch, and may be, for example, a pressure-sensitive (resistive) or proximity (capacitive) touch panel switch. In addition, the operation unit 52 may include a microphone (not shown) to input a blood pressure measurement start instructions in response to the user's voice.

The memory 51 non-transitorily stores data of a program for controlling the sphygmomanometer 1, data used for controlling the sphygmomanometer 1, setting data for setting various functions of the sphygmomanometer 1, data of measurement results of blood pressure values, and the like. In addition, the memory 51 is used as a work memory or the like when a program is executed.

The CPU 100 executes various functions as a control unit in accordance with a program for controlling the sphygmomanometer 1 stored in the memory 51. For example, when blood pressure measurement is performed by oscillometric method, the CPU 100 performs control to drive the pump 32 (and the valve 33) based on a signal from the pressure sensor 31 in response to instructions to start blood pressure measurement from the operation unit 52. In addition, the CPU 100 performs control to calculate the blood pressure value based on the signal from the pressure sensor 31 in this example.

The communication unit 59 is controlled by the CPU 100 to transmit predetermined information to an external device via the network 900, receives information from an external device via the network 900, and delivers the information to the CPU 100. The communication via the network 900 may be wireless or wired. In this embodiment, the network 900 is the Internet, but is not limited thereto, and may be another type of network such as a hospital local area network (LAN), or may be one-to-one communication using a USB cable or the like. The communication unit 59 may include a micro USB connector.

The pump 32 and the valve 33 are connected to the pressing cuff 21 via the air pipe 39, and the pressure sensor 31 is connected to the pressing cuff 21 via the air pipe 38. It should be noted that the air pipes 39 and 38 may be one common pipe. The pressure sensor 31 detects the pressure in the pressing cuff 21 via the air pipe 38. The pump 32 includes a piezoelectric pump in this example and supplies air as a fluid for pressurization to the pressing cuff 21 through the air pipe 39 in order to raise the pressure in the pressing cuff 21 (cuff pressure). The valve 33 is mounted on the pump 32, and is configured to be controlled in opening/closing as the pump 32 is turned on/off. That is, when the pump 32 is turned on, the valve 33 closes and air is filled into the pressing cuff 21, while when the pump 32 is turned off, the valve 33 opens and the air in the pressing cuff 21 is discharged into the atmosphere through the air pipe 39. It should be noted that the valve 33 has a function of a check valve so that the discharged air does not flow back. The pump drive circuit 320 drives the pump 32 based on a control signal supplied from the CPU 100.

The pressure sensor 31 is a piezoresistive pressure sensor in this example, and detects the pressure of the belt 20 (pressing cuff 21), a pressure with the atmospheric pressure as a reference (zero) in this example, through the air pipe 38 to output the detected result as a time-series signal. The oscillation circuit 310 oscillates based on an electrical signal value based on a change in electrical resistance due to the piezoresistive effect from the pressure sensor 31, and outputs a frequency signal having a frequency corresponding to the electrical signal value of the pressure sensor 31 to the CPU 100. In this example, the output of pressure sensor 31 is used for controlling the pressure of the pressing cuff 21, and for calculating the blood pressure value (including systolic blood pressure (SBP) and diastolic blood pressure (DBP)) by oscillometric method.

The battery 53 supplies power to elements mounted on the main body 10, in this example, to each element of the CPU 100, the pressure sensor 31, the pump 32, the valve 33, the display 50, the memory 51, the communication unit 59, the oscillation circuit 310, and the pump drive circuit 320. In addition, the battery 53 also supplies power to the energization and voltage detection circuit 49 of the impedance measurement unit 40 through the wiring line 71. This wiring line 71 is provided to extend between the main body 10 and the impedance measurement unit 40 along the circumferential direction of the belt 20 in a state of being sandwiched between the strip 23 of the belt 20 and the pressing cuff 21 together with the signal wiring line 72.

Figure 5A:
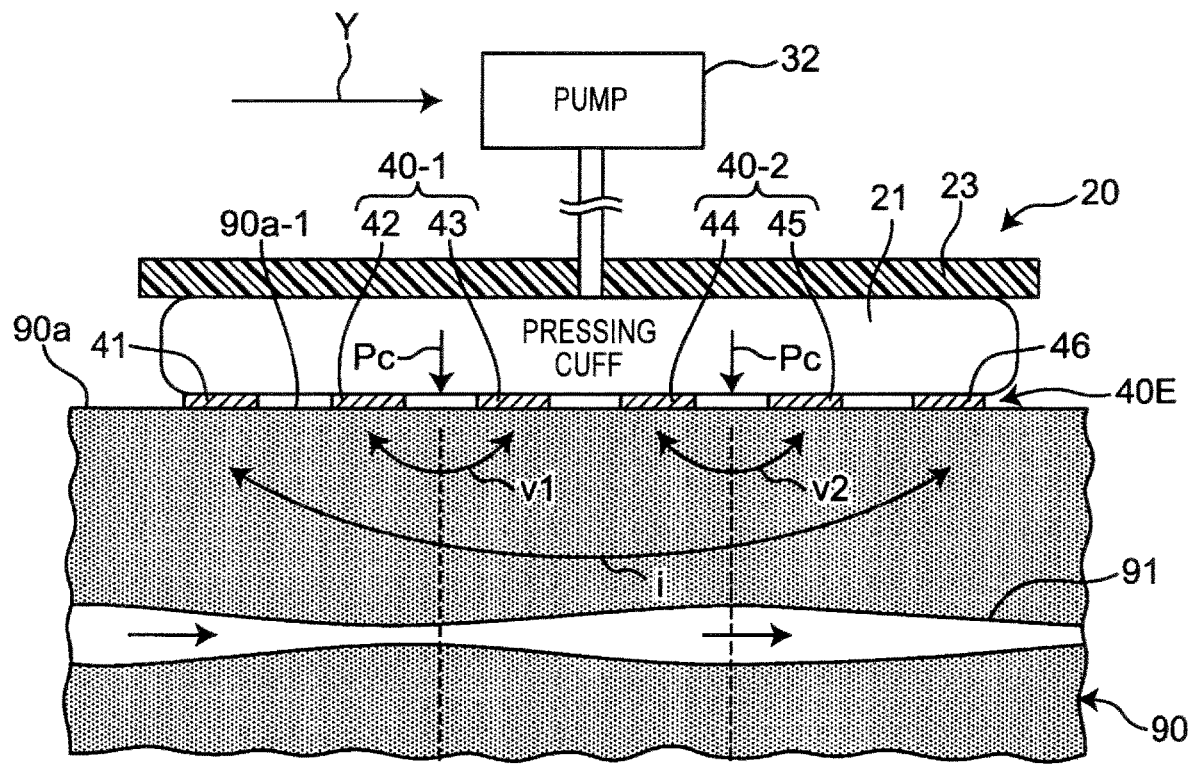
FIG. 5A is a diagram schematically illustrating a cross section along the longitudinal direction of the wrist in a state where the sphygmomanometer is mounted on the left wrist.
Figure 5B:
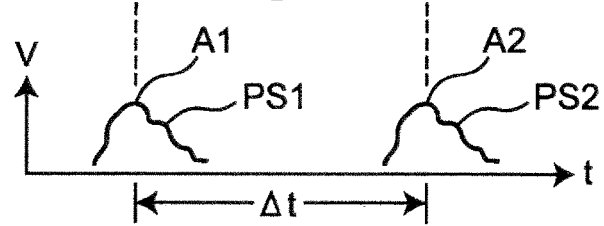
FIG. 5B is a diagram illustrating waveforms of first and second pulse wave signals respectively output from the first and second pulse wave sensors.

The energization and voltage detection circuit 49 of the impedance measurement unit 40 is controlled by the CPU 100, and supplies a high frequency constant current i having a frequency of 50 kHz and a current value of 1 mA, in this example, between the current electrode pair 41 and 46 disposed on both sides in the longitudinal direction of the wrist (corresponding to the width direction Y of the belt 20) during the operation, as illustrated in FIG. 5A. In this state, the energization and voltage detection circuit 49 detects a voltage signal v1 between the first detection electrode pair 42 and 43 forming the first pulse wave sensor 40-1 and a voltage signal v2 between the second detection electrode pair 44 and 45 forming the second pulse wave sensor 40-2. These voltage signals v1 and v2 respectively represent the change in the electrical impedance due to the pulse wave of the blood flow of the radial artery 91 in the portions where the first pulse wave sensor 40-1 and the second pulse wave sensor 40-2 face on the palmar surface 90a of the left wrist 90 (impedance system). The energization and voltage detection circuit 49 rectifies, amplifies, and filters these voltage signals v1 and v2 to output a first pulse wave signal PS1 and a second pulse wave signal PS2 having mountain-shaped waveforms in time series as illustrated in FIG. 5B. In this example, the voltage signals v1 and v2 are approximately 1 mV. In addition, the respective peaks A1 and A2 of the first pulse wave signal PS1 and the second pulse wave signal PS2 are approximately 1 volt in this example.

It should be noted that assuming that the pulse wave velocity (PWV) of the blood flow of the radial artery 91 is in the range of 1000 cm/s to 2000 cm/s, since the substantial space D between the first pulse wave sensor 40-1 and the second pulse wave sensor 40-2 is 20 mm, the time difference Δt between the first pulse wave signal PS1 and the second pulse wave signal PS2 is in the range of 1.0 ms to 2.0 ms.

(Operation of Blood Pressure Measurement by Oscillometric Method)

Figure 6:
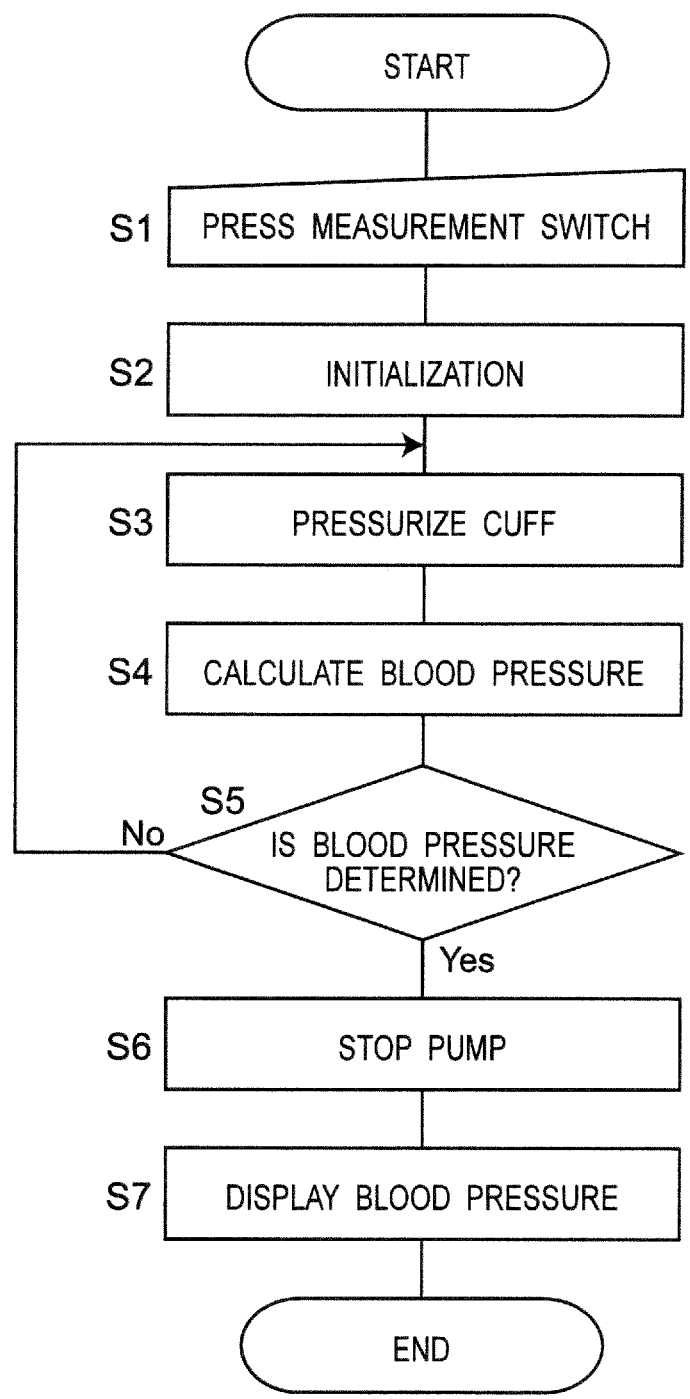
FIG. 6 is a diagram illustrating an operation flow when the sphygmomanometer performs blood pressure measurement by oscillometric method.

FIG. 6 illustrates an operation flow when the sphygmomanometer 1 performs blood pressure measurement by oscillometric method.

When the user instructs blood pressure measurement by oscillometric method with the push switch as the operation unit 52 provided in the main body 10 (step S1), the CPU 100 starts operation to initialize the processing memory area (step S2). In addition, the CPU 100 turns off the pump 32 via the pump drive circuit 320, opens the valve 33, and discharges the air in the pressing cuff 21. Subsequently, control is performed to set the current output value of the pressure sensor 31 as a value corresponding to the atmospheric pressure (0 mmHg adjustment).

Subsequently, the CPU 100 operates as a pressure control unit to close the valve 33, and then drives the pump 32 via the pump drive circuit 320 to perform control to send air to the pressing cuff 21. Thus, the pressing cuff 21 is inflated and the cuff pressure Pc (see FIG. 7) is gradually raised (step S3 in FIG. 6).

Figure 7:
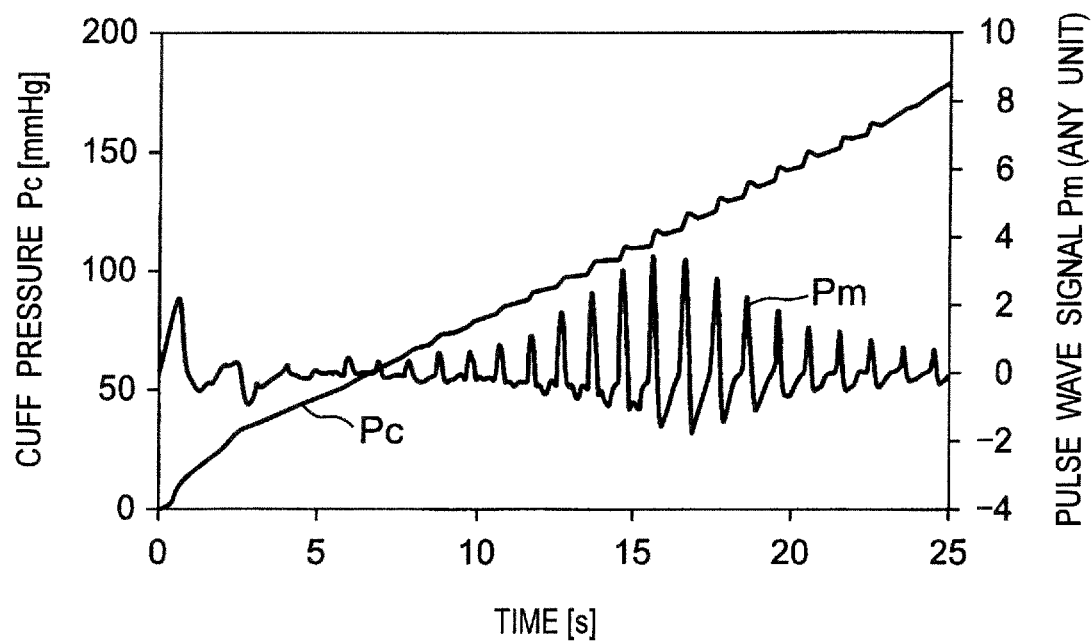
FIG. 7 is a diagram illustrating changes in a cuff pressure and a pulse wave signal according to the operation flow in FIG. 6.

In this pressurization process, the CPU 100 monitors the cuff pressure Pc with the pressure sensor 31 in order to calculate the blood pressure value, and acquires, as a pulse wave signal Pm as illustrated in FIG. 7, the fluctuation component of the arterial volume generated in the radial artery 91 of the left wrist 90 as the measurement site.

Next, in step S4 in FIG. 6, the CPU 100 acts as a second blood pressure calculation unit, and applies a known algorithm by oscillometric method based on the pulse wave signal Pm acquired at this time to attempt the calculation of blood pressure values (systolic blood pressure SBP and diastolic blood pressure DBP).

At this time, if the blood pressure value cannot be calculated yet because of insufficient data (NO in step S5), unless the cuff pressure Pc reaches the upper limit pressure (for safety, for example, 300 mmHg is predetermined), the processing of steps S3 to S5 is repeated.

If the blood pressure value can be calculated in this manner (YES in step S5), the CPU 100 stops the pump 32, opens the valve 33, and performs control to discharge the air in the pressing cuff 21 (step S6). Then, lastly, the measurement result of the blood pressure value is displayed on the display 50 and recorded in the memory 51 (step S7).

It should be noted that the calculation of the blood pressure value may be performed not only in the pressurization process, but also in the depressurization process.

(Calibration of Blood Pressure Measurement Based on Pulse Transit Time)

In addition to the above-described blood pressure measurement by oscillometric method, the sphygmomanometer 1 also performs blood pressure measurement based on pulse transit time (PTT). The blood pressure measurement based on pulse transit time calculates blood pressure by using a correspondence equation between pulse transit time and blood pressure as described below, and the correspondence relationship between pulse transit time and blood pressure is considered to change depending on changes in measurement conditions, environment, and the like (such as the subject (user) moving from indoor to outdoor). In such a case, while it is necessary to perform the calibration (update) of the corresponding equation sequentially, in the conventional calibration method, there is a problem that it is difficult to perform calibration immediately because the burden on the user becomes excessive or time is spent during calibration.

Figure 9:
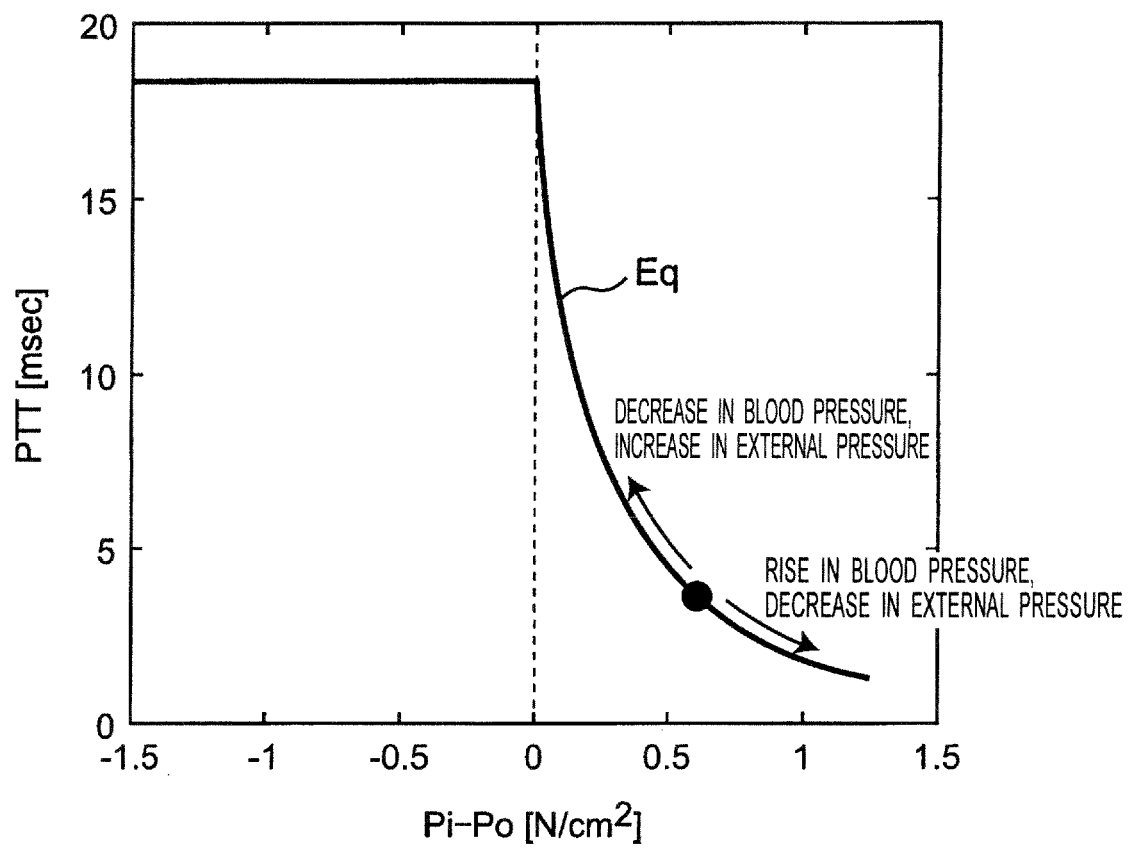
FIG. 9 is a graph illustrating a correspondence equation between pulse transit time and blood pressure in the sphygmomanometer.

Here, FIG. 9 illustrates the correspondence equation between the pulse transit time and the blood pressure in the sphygmomanometer 1. In FIG. 9, the vertical axis represents pulse transit time (PTT), and the horizontal axis represents internal-external pressure difference (Pi−Po). The graph in FIG. 9 exemplifies the correspondence equation of exponential function represented by the following equation (Eq).

[Mathematical Equation 1]

$$PTT = a \cdot \exp[-b(Pi-Po)] + c \quad (Eq)$$

In the above equation (Eq), PTT is a pulse transit time, a, b, and c are coefficients (parameters), and exp[ ] is an exponential function. A specific functional form representing a correspondence equation such as the above equation (Eq) is prestored in, for example, the memory 51 in the sphygmomanometer 1.

The present inventor has conducted intensive studies to solve the above problems, and focused on a phenomenon in which the pulse transit time changes when the pressing force by the cuff or the like changes even when the user's blood pressure is constant (see Non-Patent Literature 1). As a result of intensive studies, the present inventor has conceived a method in which, on the basis of the above phenomenon, by measuring the pulse transit time while changing the pressing force by the pressing cuff 21 of the sphygmomanometer 1, the correspondence equation between the pulse transit time and the blood pressure is immediately calibrated. According to this method, it is possible to perform the calibration of the correspondence equation in a short time without placing an excessive burden on the user as in the conventional method. The operation of the sphygmomanometer 1 for performing the above calibration will be described below with reference to FIG. 8.

Figure 8:
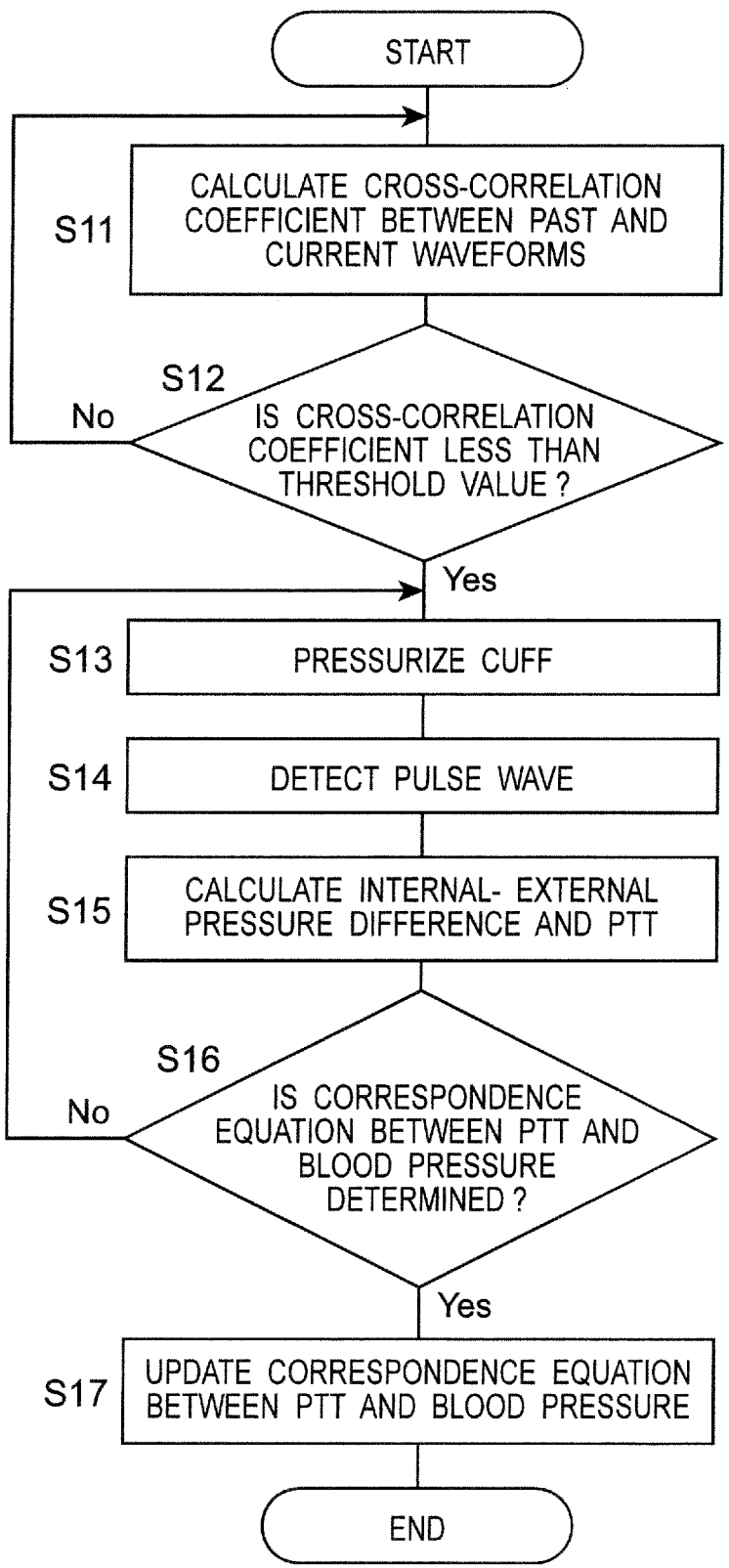
FIG. 8 is a diagram illustrating an operation flow of processing of performing calibration of blood pressure measurement based on pulse transit time in the sphygmomanometer.

FIG. 8 illustrates an operation flow of the processing of calibrating the blood pressure measurement based on the pulse transit time in the sphygmomanometer 1. The operation flow in FIG. 8 is executed by the CPU 100 functioning as a calibration processing unit. This operation flow is started in the sphygmomanometer 1 in a state where the pressing force by the pressing cuff 21 is set to a predetermined cuff pressure Pc.

In addition, it is assumed that the waveform data of the pulse wave in the past and the blood pressure value Pi are stored in advance in the memory 51 at the start time of the operation flow in FIG. 8. The waveform data of the pulse wave in the past is, for example, data indicating with a time-series data sequence {xi} the waveform of the pulse wave when the calibration of the corresponding equation is performed last time (see FIG. 12). In addition, as the blood pressure value Pi, for example, it is assumed that the value of the blood pressure measured by oscillometric method or the like on and after the previous calibration is stored.

In the operation flow in FIG. 8, the processing in steps S11 to S12 is processing for trigger determination of the timing of executing the calibration of the correspondence equation between the pulse transit time and the blood pressure. First, the CPU 100 calculates a cross-correlation coefficient r between the waveform of the past pulse wave (previous calibration of the corresponding equation is made) and the waveform of the current pulse wave (step S11).

In step S11, the CPU 100 acquires, for example, the first pulse wave signal PS1 output by the first pulse wave sensor 40-1 in time series, and generates waveform data of the current pulse wave in which the waveform of the acquired first pulse wave signal PS1 is indicated by a data sequence {yi}. Then, the CPU 100 refers to the waveform data of the past pulse wave stored in the memory 51, and uses, for example, the equation (Eq. 1) in FIG. 12 to calculate a cross-correlation coefficient r based on the data sequences {xi} and {yi} of waveform data of the past and the current pulse waves. It should be noted that the waveform data of the current pulse wave may be generated by using the second pulse wave signal PS2 from the second pulse wave sensor 40-2 instead of the first pulse wave signal PS1.

Next, the CPU 100 determines whether the calculated cross-correlation coefficient r is less than a predetermined first threshold value (referred to as α1) (step S12). The threshold value α1 in step S12 is a reference value for detecting that the current waveform and the past waveform of the pulse wave are non-identical, and is set appropriately from the viewpoint of the similarity between the waveforms considered to be identical to each other. In this example, the threshold value α1 is assumed to be set as α1=0.99.

When the calculated cross-correlation coefficient r is the threshold value α1 or more (NO in step S12), since the current pulse wave waveform is not deviated from the past waveform to the extent of being considered non-identical, the CPU 100 periodically repeats the processing in and after step S11 particularly without changing the current correspondence equation. Thus, the deviation of the current waveform from the past pulse wave is monitored in real time while the cross-correlation coefficient r is not below the threshold value α1.

When the calculated cross-correlation coefficient r becomes less than the threshold value α1 (YES in step S12), the CPU 100 updates the waveform data of the past pulse wave stored in the memory 51 based on the pulse wave when, for example, the cross-correlation coefficient r falls below the threshold value α1, and the CPU 100 proceeds to step S13. The processing in steps S13 to S17 is processing of executing calibration of the correspondence equation between the pulse transit time and the blood pressure to update the correspondence equation to a new correspondence equation corresponding to the current measurement condition.

In steps S13 to S17 in FIG. 8, first, the CPU 100 changes the cuff pressure Pc of the pressing cuff 21 with, for example, pressurization (step S13). Specifically, the CPU 100 drives the pump 32 via the pump drive circuit 320 to perform control to send air to the pressing cuff 21. Thus, the pressing cuff 21 is inflated and the cuff pressure Pc (see FIG. 5A) is raised to a specific pressure value Po. The pressurization control in step S13 may be performed in stages for each pressure value Po set in advance, or may be performed continuously while the pressure value Po is monitored by the pressure sensor 31.

Next, the CPU 100 acquires first and second pulse wave signals PS1 and PS2 respectively output in time series from the first and second pulse wave sensors 40-1 and 40-2, and detects a pulse wave at a specific pressure value Po (step S14).

Next, the CPU 100 calculates a pulse transit time based on a pulse wave at a specific pressure value Po and an internal-external pressure difference (step S15). The internal-external pressure difference is the difference between the internal pressure and the external pressure of the blood vessel wall of the artery at the measurement site. Specifically, in step S15, the CPU 100 calculates a time difference Δt between the acquired first pulse wave signal PS1 and the second pulse wave signal PS2 as a pulse transit time (PTT) (see FIG. 5B). In addition, the CPU 100 refers to the blood pressure value Pi stored in the memory 51, and calculates the difference (Pi−Po) between the referred blood pressure value Pi and the specific pressure value Po as the internal-external pressure difference.

Based on the calculation result of the pulse transit time and the internal-external pressure differences in step S15, the CPU 100 attempts to adjust various coefficients in the corresponding equation, and determines whether the correspondence equation of the calibration result can be determined (step S16). For example, when calculating the pulse transit time and the internal-external pressure difference for the first time, the CPU 100 proceeds to "NO" in step S16, and executes the processing in and after step S13 at a larger pressure value Po. Repeating steps S13 to S16 allows a data set in which the pulse transit time (PTT) and the internal-external pressure difference (Pi−Po), calculated at a plurality of pressure values Po, are associated with each other to be obtained.

The processing of determining the correspondence equation of the calibration result in step S16 is performed by, for example, curve fitting. The details in step S16 will be described with reference to FIG. 9.

According to the equation (Eq) already described, the blood pressure value Pi is included in the correspondence equation as internal-external pressure difference (Pi−Po), and as illustrated in FIG. 9, increase in blood pressure value Pi corresponds to decrease in pressure value Po, and decrease in blood pressure value Pi corresponds to increase in pressure value Po. From this, in a data set in a resting state obtained in steps S13 to S16 in FIG. 8 (blood pressure value Pi fixed) and at a plurality of pressure values Po, the data at large pressure value Po is plotted in the same way as in a state where the blood pressure value Pi decreases on the graph in FIG. 9. In addition, the data at the small pressure value Po substitutes for the state in which the blood pressure value Pi of the user is increased.

With respect to the data set obtained in steps S13 to S16 as described above, in step S16 in FIG. 8, the CPU 100 executes fitting based on the function form stored in the memory 51 by using a known method such as (non-linear) least square method. For example, the CPU 100 performs fitting of the equation (Eq) to attempt to derive the coefficients a, b, and c, and when the coefficients a, b, and c are obtained, the CPU 100 proceeds to "YES" in step S16. In addition, if the coefficients a, b, and c are not obtained due to a fitting error or the like, the CPU 100 proceeds to "NO" in step S16, and collects a data set again.

If determining that the correspondence equation based on the equation (Eq) is determined by, for example, deriving the coefficients a, b, and c (YES in S16), the CPU 100 records the values of the obtained coefficients a, b and c in the memory 51, and updates the correspondence equation to be used at the time of blood pressure measurement based on the pulse transit time (step S17).

The CPU 100 ends the operation flow in FIG. 8 by updating the correspondence equation in step S17.

According to the above processing, in the calibration of the correspondence equation between the pulse transit time and the blood pressure, using the pulse transit time corresponding to a plurality of pressure values Po (steps S13 to S16) allows the calibration to be easily performed without placing a burden of changing the blood pressure value Pi on the user.

In addition, in the processing in steps S11 and S12, performing trigger determination based on whether the past and current pulse wave waveforms are not identical immediately executes the calibration of the above correspondence equation according to the change in the measurement condition such that the waveform of the pulse wave is deviated and allows the measurement accuracy of the blood pressure using the correspondence equation to be easily secured. It should be noted that although the cross-correlation coefficient r is used in steps S11 and S12 in FIG. 8, the trigger determination of the calibration of the corresponding equation may be performed by various methods as described below.

In the above description, the blood pressure value Pi stored in advance in the memory 51 is used when the internal-external pressure difference (Pi−Po) is calculated, but the present invention is not limited thereto, and for example, blood pressure measurement by oscillometric method may be performed at the start of calibration. For example, the CPU 100 may acquire the blood pressure value Pi by performing the same processing as steps S3 to S6 in FIG. 6 between step S12 and step S13 in FIG. 8.

In addition, in the above description, an example in which the pressure value Po of the pressing cuff 21 is changed by pressurization in step S13 is described, but the pressure value Po may be changed not only by pressurization but also by depressurization.

In addition, in the above description, the correspondence equation of the calibration result is determined by fitting in step S16, but the method of determining the calibration result is not particularly limited thereto. For example, equivalently to this, the CPU 100 may substitute the calculation result in step S15 into a function form such as the equation (Eq) and solve simultaneous equations having the coefficients a, b, and c as variables.

In addition, in the above description, a function form of an exponential type correspondence equation such as the equation (Eq) is used, but the function form of the correspondence equation is not limited to an exponential function type, and various function forms such as a polynomial type may be used.

(Operation of Blood Pressure Measurement Based on Pulse Transit Time)

The operation of performing the blood pressure measurement based on the pulse transit time using the correspondence equation calibrated as described above will be described with reference to FIG. 10.

Figure 10:
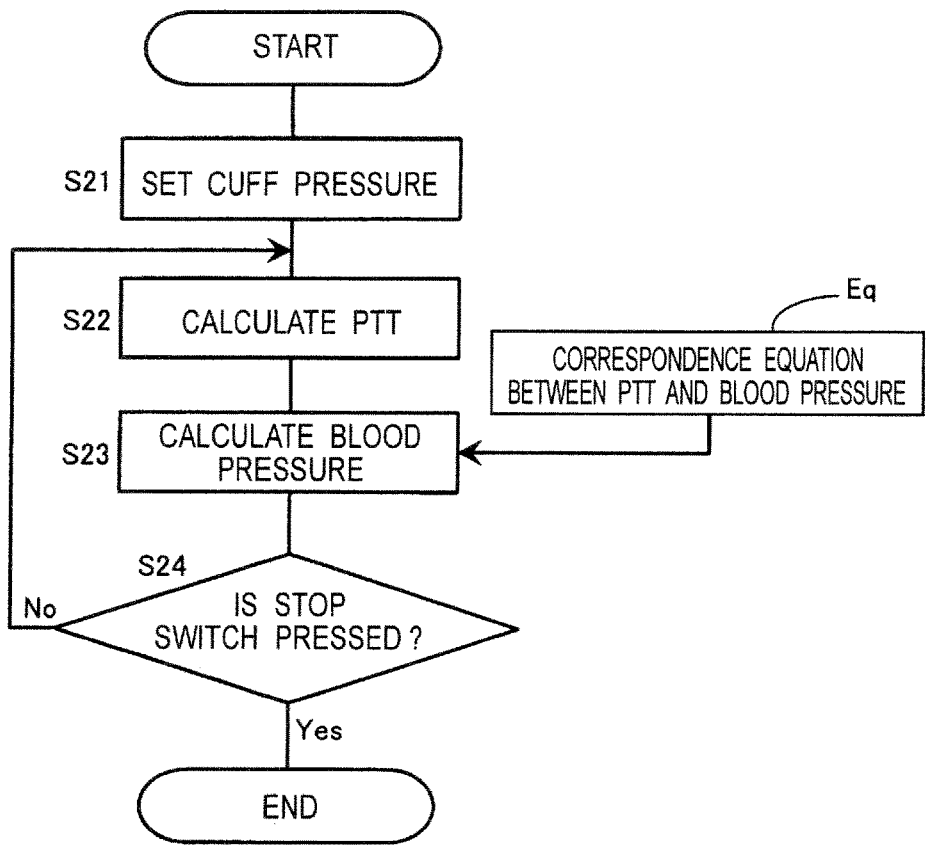
FIG. 10 is a diagram illustrating an operation flow when the sphygmomanometer executes the blood pressure measurement method of one embodiment to perform blood pressure measurement (estimation) based on pulse transit time.

FIG. 10 is a diagram illustrating an operation flow when the sphygmomanometer 1 executes the blood pressure measurement method according to one embodiment to perform blood pressure measurement (estimation) based on the pulse transit time. The operation flow in FIG. 10 is performed by the CPU 100 of the sphygmomanometer 1 after the execution of the operation flow in FIG. 8, for example.

In the operation flow in FIG. 10, first, the CPU 100 controls each portion in the sphygmomanometer 1 so that the pressing force by the pressing cuff 21 is in the state of the cuff pressure Pc set in advance (step S21).

In this state, the CPU 100 works as a measurement processing unit to acquire the time difference Δt between the first and second pulse wave signals PS1 and PS2 (see FIG. 5B) as a pulse transit time (PTT) (step S22). More specifically, in this example, a time difference Δt between the peak A1 of the first pulse wave signal PS1 and the peak A2 of the second pulse wave signal PS2 is acquired as a pulse wave propagation time (PTT).

Next, the CPU 100 works as a first blood pressure calculation unit, and calculates (estimates) the blood pressure based on the pulse transit time acquired in step S22 by using the predetermined correspondence equation Eq between pulse transit time and blood pressure (step S23). At this time, the CPU 100 as the first blood pressure calculation unit refers to the information stored in the memory 51, and uses the correspondence equation Eq updated as the calibration processing unit. Thus, in step S23, the blood pressure is calculated as needed by using the correspondence equation Eq calibrated according to the measurement conditions.

In the operation example in FIG. 10, if measurement stop is not instructed by the push switch as the operation unit 52 in step S24 (NO in step S24), the pulse transit time calculation (step S22) and the blood pressure calculation (estimation) (step S23) are periodically repeated every time the first and second pulse wave signals PS1 and PS2 are input according to the pulse wave. The CPU 100 updates and displays the measurement result of the blood pressure value on the display 50, and accumulates and records the measurement result in the memory 51. Then, if measurement stop is instructed in step S24 in FIG. 8 (YES in step S24), the measurement operation based on the pulse transit time is ended.

According to this sphygmomanometer 1, the blood pressure measurement based on the pulse transit time (PTT) as described above allows blood pressure to be measured continuously over a long period of time with a reduced physical burden on the user.

In addition, according to the sphygmomanometer 1, the blood pressure measurement (estimation) based on pulse transit time and the blood pressure measurement by oscillometric method can be performed by an integrated device. Therefore, the convenience of the user can be enhanced.

(Verification of Effect)

Verification of the effect of the calibration of the correspondence equation when blood pressure measurement based on the pulse transit time as described above is performed will be described with reference to FIGS. 11A and 11B.

Figure 11A:
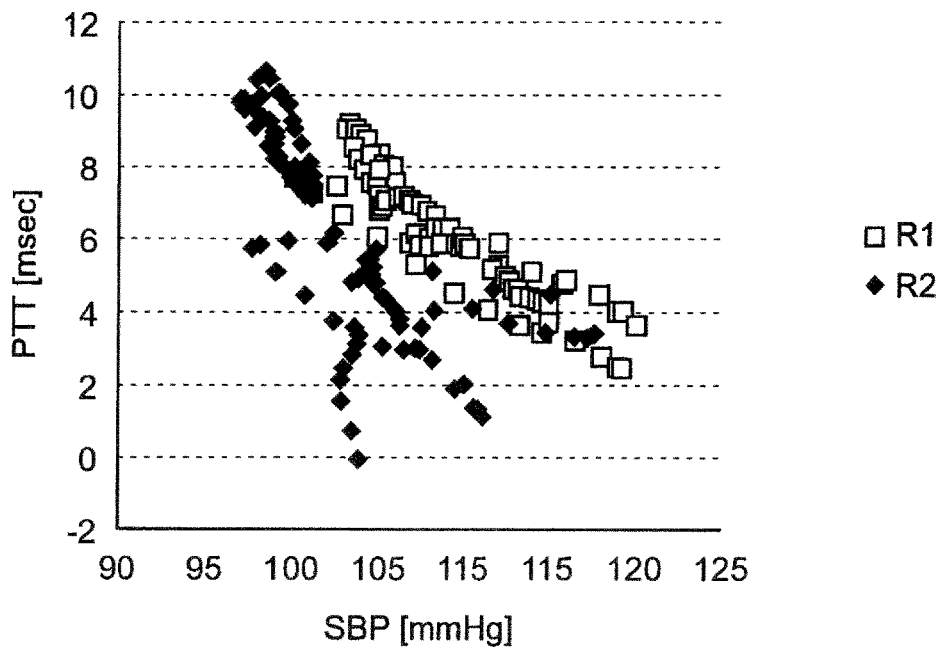
FIG. 11A is a scatter diagram illustrating a relationship between blood pressure and pulse transit time measured under different measurement conditions on the same subject.

FIG. 11A is a scatter diagram illustrating a relationship between blood pressure (SBP) and pulse transit time (PTT) measured under different measurement conditions (R1, R2) on the same subject. The □ mark in the drawing indicates data under the first measurement condition R1. In addition, the ⎣ mark indicates data under the second measurement condition R2. As illustrated in FIG. 11A, even on the same subject, the manner of distribution is different between the blood pressure and pulse transit time measured under the first measurement condition R1 and the blood pressure and pulse transit time measured under the second measurement condition R2 different from the first measurement condition R1. Thus, even on the same subject, change in the measurement conditions changes the correspondence relationship between the blood pressure and the pulse transit time.

FIG. 11B is a scatter diagram illustrating distribution of estimation errors corresponding to the presence or absence of calibration of the correspondence equation when the measurement conditions change. The estimation error is an error of the blood pressure calculated (estimated) based on the pulse transit time using the correspondence equation with respect to the actual blood pressure. The □ mark in the drawing indicates data in a case where calibration is performed when the measurement conditions change, and the ♦ mark indicates data in a case where no such calibration is performed. That is, in the drawing, in the state where the second measurement condition R2 is changed to the first measurement condition R1, the estimation error (□ mark) when the correspondence equation calibrated under the second measurement condition R2 is recalibrated according to the first measurement condition R1, and the estimation error (♦ mark) when the correspondence equation is not recalibrated are illustrated.

According to FIG. 11B, the estimation error when the correspondence equation is recalibrated is obviously smaller than the estimation error when the recalibration is not performed. Thus, sequentially performing (re) calibration of the correspondence equation when the measurement conditions change makes it possible to confirm that the accuracy of the blood pressure measurement based on the pulse transit time is improved.

(Modification)

In the above embodiment, in the trigger determination (steps S11 and S12 in FIG. 8) for performing the calibration of the correspondence equation between the pulse transit time and the blood pressure, the cross-correlation coefficient r is used to determine whether the past and the current waveforms are not identical. Not limited to this, and for example, the plethysmogram area ratio VR may be used. The plethysmogram area ratio VR is expressed as the following equation (Eq. 2) by using a plethysmogram area (area occupied by a pulse wave of one beat) S as illustrated in FIG. 13, a cardiac cycle (one period of a heartbeat) RR, and a pulse wave amplitude L.

[Mathematical Equation 2]

$$VR = S/(RR \times L) \qquad \text{(Eq. 2)}$$

For example, in the operation flow in FIG. 8, instead of the determination in step S12, the CPU 100 determines whether the ratio between the past plethysmogram area ratio VR1 and the current plethysmogram area ratio VR2 exceeds a predetermined second threshold value (α2), and when the ratio exceeds the threshold value α2, the CPU 100 proceeds to step S13. In this case, the plethysmogram area ratio VR1 at the time of the previous calibration (past) is stored in the memory 51 instead of the past waveform data. In addition, instead of step S11, the CPU 100 calculates the current plethysmogram area ratio VR2 from the first or second pulse wave signal SP1 or SP2. For example, when the ratio VR1/VR2 exceeds the upper limit threshold value α2=1.4 or falls below the lower limit threshold value α2=0.6, the CPU 100 proceeds to step S13 on the assumption that the past and current waveforms are not identical, and the calibration of the correspondence equation is performed.

In addition, the determination of whether to execute the calibration of the correspondence equation as described above may be performed based on not only the nonidentity between the past and current waveforms, but also, for example, the difference between past and current cardiac cycles RR. For example, in the operation flow in FIG. 8, instead of the determination in step S12, the CPU 100 determines whether a difference in the ratio or difference between the past cardiac cycle RR1 and the current cardiac cycle RR2 exceeds a predetermined third threshold value (α3), and if the difference exceeds the threshold value α3, the CPU 100 proceeds to step S13 to execute the calibration of the correspondence equation. In this case, the cardiac cycle RR1 at the time of the previous calibration (past) is stored in the memory 51 instead of the past waveform data. In addition, instead of step S11, the CPU 100 calculates the current cardiac cycle RR2 from the first or second pulse wave signal SP1 or SP2. In addition, the threshold value α3 is appropriately set from the viewpoint of the fluctuation of the cardiac cycle RR in which a change in the measurement conditions is assumed to occur. For example, the calibration may be performed when the difference between the past cardiac cycle RR1 and the current cardiac cycle RR2 (RR1−RR2) exceeds α3=10 beats/minute.

In addition, in the above embodiment, the trigger determination for executing calibration of the correspondence equation between pulse transit time and blood pressure is performed (steps S11 and S12 in FIG. 8), and in addition to or instead of this, detection that the user is in a resting state may be performed. For example, between the steps S12 and S13 in the operation flow in FIG. 8, the CPU 100 detects the fluctuation amount of the pulse rate based on the first and second pulse wave signals SP1 and SP2, and for example, when the standard deviation of 10 seconds comes into a state of 5 beats/minute or less, the CPU 100 proceeds to step S13.

In addition, the processing for calibration of the correspondence equation (steps S13 to S17 in FIG. 8) may be performed particularly without performance of the trigger determination, and for example, the processing in and after step S13 may be performed when instructions by the user are made via the operation unit 52.

In addition, in the above embodiment, the first pulse wave sensor 40-1 and the second pulse wave sensor 40-2 detect the pulse wave of the artery (radial artery 91) passing through the measurement site (left wrist 90) as a change in impedance (impedance system). However, the present invention is not limited thereto. Each of the first and second pulse wave sensors may include a light emitting element for applying light toward an artery passing through a corresponding portion of the measurement site and a light receiving element for receiving the reflected light (or transmitted light) of the light, and may detect a pulse wave of the artery as a change in volume (photoelectric system). Alternatively, each of the first and second pulse wave sensors may include a piezoelectric sensor abutted on the measurement site, and may detect the strain due to the pressure of the artery passing through the corresponding portion of the measurement site as a change in electrical resistance (piezoelectric system). Furthermore, each of the first and second pulse wave sensors may include a transmission element for transmitting a radio wave (transmission wave) toward an artery passing through a corresponding portion of the measurement site and a reception element for receiving the reflected wave of the radio wave, and may detect a change in the distance between the artery and the sensor due to the pulse wave of the artery as a phase deviation between the transmission wave and the reflected wave (radio wave irradiation system).

In addition, in the above embodiment, the sphygmomanometer 1 is intended to be mounted on the left wrist 90 as a measurement site. However, the present invention is not limited thereto. The measurement site has only to be a site where an artery passes through, may be an upper limb such as an upper arm other than the wrist, and may be a lower limb such as an ankle or thigh.

In addition, in the above embodiment, the CPU 100 mounted on the sphygmomanometer 1 is assumed to work as a measurement processing unit, a calibration processing unit, and first and second blood pressure calculation units to perform blood pressure measurement by oscillometric method (operation flow in FIG. 6), blood pressure measurement (estimation) based on PTT (operation flow in FIG. 10), and its calibration (operation flow in FIG. 8). However, the present invention is not limited thereto. For example, a substantial computer device such as a smartphone provided outside the sphygmomanometer 1 may work as a measurement processing unit, a calibration processing unit, and first and second blood pressure calculation units to cause the sphygmomanometer 1, via the network 900, to perform blood pressure measurement by oscillometric method (operation flow in FIG. 6), blood pressure measurement (estimation) based on PTT (operation flow in FIG. 10), and its calibration (operation flow in FIG. 8).

As described above, a blood pressure measurement device of the present disclosure comprises:

a belt to be mounted around a measurement site;

a first pulse wave sensor and a second pulse wave sensor mounted on the belt in a state of being separated from each other in a width direction of the belt, the first pulse wave sensor and the second pulse wave sensor being configured to detect pulse waves of respective portions facing the first pulse wave sensor and the second pulse wave sensor of an artery passing through the measurement site;

a measurement processing unit configured to acquire, as a pulse transit time, a time difference between a first pulse wave signal and a second pulse wave signal respectively output by the first pulse wave sensor and the second pulse wave sensor in time series;

a first blood pressure calculation unit configured to use a predetermined correspondence equation between a pulse transit time and a blood pressure to calculate a blood pressure based on a pulse transit time acquired by the measurement processing unit;

a pressing member mounted on the belt, configured to press the first pulse wave sensor and the second pulse wave sensor against the measurement site while varying a pressing force; and a calibration processing unit configured to acquire a pulse transit time with the measurement processing unit while changing a pressing force by the pressing member in a resting state to calibrate the corresponding equation based on a plurality of pulse transit times corresponding to a plurality of respective pressing forces.

In the present specification, "measurement site" refers to a site through which an artery passes. The measurement site may be, for example, an upper limb such as a wrist or an upper arm, or a lower limb such as an ankle or a thigh.

In addition, "belt" refers to a band-shaped member mounted around a measurement site regardless of the name. For example, instead of the belt, the name may be "band", "cuff", or the like.

In addition, "resting state" refers to a state in which the pulse rate (beat/minute) of the subject having the measurement site does not fluctuate excessively. For example, the resting state is a state in which the fluctuation amount of the pulse rate (for example, standard deviation of 10 seconds) is 5 beat/minute or less.

In addition, "predetermined correspondence equation between pulse transit time and blood pressure" refers to, for example, the following equation disclosed in Non-Patent Literature 1.

[Mathematical Equation 1]

$$PTT = a \cdot \exp[-b(Pi-Po)] + c \quad \text{(Eq)}$$

where PTT represents a pulse transit time, and Pi represents a blood pressure value to be calculated, Po represents a pressure value due to external pressure such as pressing force by the pressing member. a, b, and c are coefficients.

In addition, to "calibrate" the correspondence equation refers to setting the coefficients a, b, and c by using a measured pulse transit time and blood pressure value, for example, in the case of the correspondence equation (Eq) exemplified above.

In the blood pressure measurement device of the present i disclosure, calibration of the correspondence equation for measuring blood pressure based on pulse transit time is performed based on a plurality of pulse transit times obtained when the pressing force by the pressing member in the resting state is changed. Thus, the calibration when blood pressure is measured based on the pulse transit time can be easily performed without applying a load as to change the blood pressure to the subject.

In the blood pressure measurement device of one embodiment, the calibration processing unit determines whether a past waveform and a current waveform in a pulse wave detected by the first pulse wave sensor or the second pulse wave sensor are not identical, and performs calibration of the correspondence equation when determining that the past waveform and the current waveform are not identical.

"Past" and "current" refer to two time points at which the condition of the subject may change, such as the time point one hour ago and the current time point, or the time point one day ago and the current time point.

In the blood pressure measurement device of this one embodiment, the calibration of the correspondence equation is performed when the past and current waveforms in the pulse wave become non-identical. Thus, when the current waveform deviates from the past waveform, the above correspondence equation is immediately calibrated, and the measurement of blood pressure based on the pulse transit time can be accurately performed.

In the blood pressure measurement device of one embodiment, the calibration processing unit calculates a cross-correlation coefficient between the past waveform and the current waveform to determine whether the past waveform and the current waveform are not identical based on whether a calculated cross-correlation coefficient exceeds a predetermined first threshold value.

Herein, "cross-correlation coefficient" means the sample correlation coefficient (also referred to as Pearson's product-moment correlation coefficient). For example, when a data sequence $\{x_i\}$ and a data sequence $\{y_i\}$ including two sets of numerical values (where i=1, 2, . . . , n) are given, the cross-correlation coefficient r between the data sequence $\{x_i\}$ and the data sequence $\{y_i\}$ is defined by the equation (Eq. 1) illustrated in FIG. 12. In the equation (Eq. 1), x and y with overlines respectively represent average values of x and y.

In the blood pressure measurement device of this one embodiment, the determination as to whether the past and current waveforms are not identical is performed based on the cross-correlation coefficient between the past and current waveforms. Thus, it is possible to easily detect that the current waveform deviates from the past waveform and to easily secure the measurement accuracy of the blood pressure.

In the blood pressure measurement device of one embodiment, the calibration processing unit calculates a plethysmogram area ratio based on a waveform of a pulse wave detected by the first pulse wave sensor or the second pulse wave sensor, and determines that the past waveform and the current waveform are not identical if a ratio between a calculated plethysmogram area ratio and a past plethysmogram area ratio exceeds a predetermined second threshold value.

Herein, "plethysmogram area ratio" refers to the ratio of the plethysmogram area to the product of the pulse wave amplitude and the cardiac cycle.

In the blood pressure measurement device of this one embodiment, the determination as to whether the past and current waveforms are not identical is performed by comparing the past and current plethysmogram area ratios. Also with this, it is possible to easily detect that the current waveform deviates from the past waveform and to easily secure the measurement accuracy of the blood pressure.

In the blood pressure measurement device of one embodiment, the calibration processing unit calculates a cardiac cycle based on a pulse wave detected by the first pulse wave sensor or the second pulse wave sensor, and performs calibration of the correspondence equation if difference between a calculated cardiac cycle and a past cardiac cycle exceeds a predetermined third threshold value.

In the blood pressure measurement device of this one embodiment, the calibration of the correspondence equation is performed based on the difference between the current and past cardiac cycles. Thus, it is possible to detect the change in the measurement condition based on the difference in the cardiac cycle and to easily secure the measurement accuracy of the blood pressure.

In the blood pressure measurement device of one embodiment,
the pressing member is a fluid bag provided along the belt,
the blood pressure measurement device further comprises a main body provided integrally with the belt, and
on the main body, the measurement processing unit, the first blood pressure calculation unit, and the calibration processing unit are mounted, and a pressure control unit configured to supply air to the fluid bag to control pressure, and a second blood pressure calculation unit configured to calculate a blood pressure based on pressure in the fluid bag are mounted for blood pressure measurement by oscillometric method.

Herein, the main body being "integrally provided" with respect to the belt may mean that the belt and the main body are, for example, integrally molded, or instead of this, may mean that the belt and the main body may be separately formed, and the main body may be integrally attached to the belt via an engaging member (for example, a hinge or the like).

In the blood pressure measurement device of this one embodiment, the blood pressure measurement (estimation) based on pulse transit time and the blood pressure measurement by oscillometric method can be performed by an integrated device. Therefore, the convenience of the user is enhanced.

In another aspect, a blood pressure measurement method of the present disclosure is a blood pressure measurement method includes:

using
a belt to be mounted around a measurement site,
a first pulse wave sensor and a second pulse wave sensor mounted on the belt in a state of being separated from each other in a width direction of the belt, the first pulse wave sensor and the second pulse wave sensor being configured to detect pulse waves of respective portions facing the first pulse wave sensor and the second pulse wave sensor of an artery passing through the measurement site, and
a pressing member mounted on the belt, configured to press the first pulse wave sensor and the second pulse wave sensor against the measurement site while varying a pressing force,
to measure a blood pressure based on a pulse wave of the measurement site, the blood pressure measurement method comprising:
acquiring, as a pulse transit time, a time difference between a first pulse wave signal and a second pulse wave signal respectively output by the first pulse wave sensor and the second pulse wave sensor in time series while changing a pressing force by the pressing member in a resting state;
calibrating a predetermined correspondence equation between a pulse transit time and a blood pressure based on a plurality of pulse transit times corresponding to a plurality of respective pressing forces; and
calculating a blood pressure based on the pulse transit time by using the correspondence equation.

According to the blood pressure measurement method of the present disclosure, it is possible to facilitate calibration when blood pressure is measured based on pulse transit time.

The above embodiments are illustrative, and various modifications can be made without departing from the scope of the present invention. It is to be noted that the various embodiments described above can be appreciated individually within each embodiment, but the embodiments can be combined together. It is also to be noted that the various features in different embodiments can be appreciated individually by its own, but the features in different embodiments can be combined.

The invention claimed is:

1. A blood pressure measurement device comprising:
a belt configured to be mounted around a measurement site;
a first pulse wave sensor and a second pulse wave sensor mounted on the belt and separated from each other in a width direction of the belt, the first pulse wave sensor and the second pulse wave sensor being configured to detect pulse waves of respective portions of an artery passing through the measurement site facing the first pulse wave sensor and the second pulse wave sensor;
a pressing member having an inflatable and/or deflatable structure mounted on the belt, configured to press the first pulse wave sensor and the second pulse wave sensor against the measurement site while varying a pressing force; and
a processor programmed to:
acquire, as a pulse transit time, a time difference between a first pulse wave and a second pulse wave signal respectively output by the first pulse wave sensor and the second pulse wave sensor in time series,
use a predetermined correspondence equation between pulse transit time and blood pressure to calculate a blood pressure based on the pulse transit time acquired by the processor,
detect a fluctuation amount of a pulse rate based on the first and second pulse wave signals and determine whether a subject is in a resting state, and
in response to determining that the subject is in the resting state, acquire a plurality of pulse transit times, each corresponding to the pressing force, while changing the pressing force by the pressing member, and calibrate the correspondence equation based on the plurality of pulse transit times corresponding to a plurality of respective pressing forces.

2. The blood pressure measurement device according to claim 1, wherein the processor is further programmed to calculate a cross-correlation coefficient between a past waveform and a current waveform in a pulse wave detected by the first pulse wave sensor or the second pulse wave sensor to determine whether the past waveform and the current waveform are not identical based on whether the calculated cross-correlation coefficient exceeds a predetermined first threshold value.

3. The blood pressure measurement device according to claim 1, wherein the processor is further programmed to calculate a plethysmogram area ratio based on a past waveform and a current waveform in a pulse wave detected by the first pulse wave sensor or the second pulse wave sensor, and determine that the past waveform and the current waveform are not identical if a ratio between the calculated plethysmogram area ratio and a past plethysmogram area ratio exceeds a predetermined second threshold value.

4. The blood pressure measurement device according to claim 1, wherein the processor is further programmed to calculate a cardiac cycle based on a pulse wave detected by the first pulse wave sensor or the second pulse wave sensor, and perform calibration of the correspondence equation if a difference between the calculated cardiac cycle and a past cardiac cycle exceeds a predetermined third threshold value.

5. The blood pressure measurement device according to claim 1, wherein
the pressing member is a fluid bag provided along the belt,
the blood pressure measurement device further comprises a main body provided integrally with the belt,
the processor is mounted on the main body, and
the processor is further programmed to supply air to the fluid bad to control pressure, and calculate blood pressure based on pressure in the fluid bag for blood pressure measurement by an oscillometric method.

6. A calibration method of a correspondence equation in a sphygmomanometer,
the sphygmomanometer comprising:
a belt configured to be mounted around a measurement site,
a first pulse wave sensor and a second pulse wave sensor mounted on the belt and separated from each other in a width direction of the belt, the first pulse wave sensor and the second pulse wave sensor being configured to detect pulse waves of respective portions of an artery passing through the measurement site facing the first pulse wave sensor and the second pulse wave sensor, and a pressing member having an inflatable and/or deflatable structure mounted on the belt, configured to press the first pulse wave sensor and the second pulse wave sensor against the measurement site while varying a pressing force, and a processor programmed to:

acquire, as a pulse transit time, a time difference between a first pulse wave signal and a second pulse wave signal respectively output by the first pulse wave sensor and the second pulse wave sensor in time series, and use a predetermined correspondence equation between pulse transit time and blood pressure to calculate a blood pressure based on the pulse transit time acquired by the processor, wherein the calibration method comprises:

detecting a fluctuation amount of a pulse rate based on the first and second pulse wave signals and determining whether a subject is in a resting state;

in response to determining that the subject is in the resting state, acquiring a plurality of pulse transit times, each corresponding to the pressing force, while changing the pressing force by the pressing member; and calibrating the correspondence equation based on the plurality of pulse transit times corresponding to a plurality of respective pressing forces.

\* \* \* \* \*